United States Patent [19]

Sasaki et al.

[11] 4,379,135

[45] Apr. 5, 1983

[54] METHOD FOR ENUMERATION OF ORAL GRAM-NEGATIVE BACTERIA

[75] Inventors: Shuji Sasaki, Odawara; Yoji Yamazaki, Kadoma, both of Japan

[73] Assignee: Lion Corporation, Tokyo, Japan

[21] Appl. No.: 307,576

[22] Filed: Oct. 1, 1981

Related U.S. Application Data

[63] Continuation of Ser. No. 18,175, Mar. 7, 1979, abandoned.

[30] Foreign Application Priority Data

Mar. 10, 1978 [JP] Japan ................................ 53-27402

[51] Int. Cl.$^3$ .................... G01N 21/64; G01N 33/54; C12Q 1/04; C12Q 1/24
[52] U.S. Cl. .............................. 436/536; 250/461.2; 424/87; 250/305; 424/92; 435/4; 435/7; 435/34; 435/822; 436/546; 436/800; 436/805; 436/825
[58] Field of Search ................... 424/8, 12, 50, 85, 87, 424/88, 92, 93; 23/230 B; 250/305, 461.2; 435/4, 7, 29, 30, 34, 822

[56] References Cited

U.S. PATENT DOCUMENTS 3,931,398  1/1976  Gaffar ................................ 424/92

OTHER PUBLICATIONS

Nairn, Fluorescent Protein Tracing, Churchill Livingstone, NY 4th Ed., 1976, pp. 163-167, 170, 171, 175-180, 185, 188, 189, 192, 193.
Stauffer, J. Clin. Microbiol. vol. 2, Oct. 1975, pp. 337-344.
Jones, Diss. Abs., vol. 35, No. 8B, p. 4018B.
Humphries, Dissertation, University Microfilms, Ann Arbor, MI, No. 71-8271, Baylor U., 1970, pp. 39-44, 104, 105.
Takeuchi, Shika Igaku, J. Osaka Odontol. Soc., vol. 33, No. 3, 1970, pp. 386-404.
Shuji Sasaki, "Biological Activity of Lipopolysaccharides Isolated from Bacteria in Human Periodontal Lesions", Nov., 1979; The Bulletin of Tokyo Dental College, vol. 20 (No. 4), pp. 159-174.
J. T. Irving et al., "Histological Changes in Experimental Periodontal Disease in Rats Monoinfected with Gram-Negative Organisms", J. Periodontal Res. 13 (Jul.): 326-332, 1978.
S. S. Socransky, "Microbiology of Periodontal Disease-Present Status and Future Considerations", J. Periodontol., vol. 48, No. 9, Sep., 1977, pp. 497-504.
J. T. Irving, International Association for Dental Research, Abstract No. 783, 1976.
S. Sasaki et al., American Association for Dental Research, Abstract No. 422, 1977.
J. T. Irving, American Association for Dental Research, Abstract No. 423, 1977.
M. G. Newman et al., "Studies of the Microbiology of Periodontosis", J. Periodontol. Jul., 1976, pp. 373-379.

Primary Examiner—Anna P. Fagelson
Attorney, Agent, or Firm—Birch, Stewart, Kolasch & Birch

[57] ABSTRACT

A reagent for the enumeration of oral gram-negative bacteria, such as *Bacteriodes melaninogenicus*, Capnocytophaga sp. and *Eikenelia corrodens*, by an indirect fluorescent antibody method is provided which utilizes an unlabelled antiserum to oral gram-negative bacteria and a fluorescent conjugated antibody obtained by immunizing an animal of a different species than the antiserum with γ-globulin of an animal of the same species as the antiserum. A sample containing oral gram-negative bacteria to be enumerated is treated with the antiserum and the reaction product obtained is then treated with the fluorescent conjugated antibody to enumerate the bacteria in the sample by observing under a fluorescent microscope.

4 Claims, No Drawings

METHOD FOR ENUMERATION OF ORAL GRAM-NEGATIVE BACTERIA

This application is a continuation of copending application Ser. No. 018,175, filed on Mar. 7, 1979, now abandoned.

BACKGROUND OF THE INVENTION

1. Field of the Invention

The present invention relates to reagents used for and methods for the enumeration of oral gram-negative bacteria, such as *Bacteroides melaninogenicus*, Capnocytophaga sp. and *Eikenella corrodens* which are related to periodontal diseases.

2. Description of the Prior Art

*Bacteroides melaninogenicus* and Capnocytophaga sp. in subgingival plaque are bacteria often studied in relation to periodontal diseases, particularly the former in relation to advanced periodontitis, and the latter to periodontosis and children's periodontal diseases. For the detection and the enumeration of these oral bacterial, an authorized method for cultivation has usually been adopted. In this method, a sample taken from a patient is incubated on a blood agar plate for about 7 days, and is then enumerated by counting special colonies—the colonies of *Bacteroides melaninogenicus* are black and those of Capnocytaphaga sp. are wet spreading—on the plate. *Eikenella corrodens*, which is also studied in relation to advanced periodontitis, is enumerated by counting colonies on a selective medium, because special colonies are not formed by the usual cultural method.

However, the method of the detection and the enumeration of the above-mentioned oral bacteria by cultivation are very complicated in operation and are very expensive. Moreover, they require a long period of time—about a week or more—for cultivation and much loss of time for the enumeration. It is, therefore, difficult to quickly and easily enumerate the oral gram-negative bacteria by adopting the usual cultural method.

SUMMARY OF THE INVENTION

It is an object of the present invention to provide a reagent for the enumeration of oral gram-negative bacteria which can detect and enumerate very efficiently bacteria such as *Bacteriodes melaninogenicus*, Capnocytophaga sp. and *Eikenella corrodens* within a shortened period of time.

A further object of the invention is to provide a reagent for the enumeration of the bacteria which can detect and enumerate the bacteria with easy operation and cheap cost.

A still further object of the invention is to provide a reagent for the enumeration of the bacteria which can detect and enumerate the bacteria with the same high precision as the usual cultural method.

According to the present invention, reagents are provided for the enumeration of bacteria related to periodontal diseases by an indirect fluorescent antibody method. An unlabelled antiserum of oral gram-negative bacteria and a fluorescent conjugated antibody are utilized. The fluorescent conjugated antibody is obtained by immunizing a different species of animal with γ-globulin of the same species of animal as the antiserum. The unlabelled antiserum is treated with a sample containing the oral gram-negative bacteria to be enumerated and then the fluorescent conjugated antibody is treated with the reaction product of the unlabelled antiserum and the sample. The resulting product is then observed under a fluorescent microscope.

By the use of the present reagent, oral gram-negative bacteria such as *Bacteroides melaninogenicus*, Capnocytophaga sp. and *Eikenella corrodens*, which are related to periodontal diseases, are detected and enumerated fast, easily and accurately. The reagent of the invention can be utilized suitably for the diagnosis and therapy of periodontal diseases, and for epidemiological studies.

The above and other objects, features and advantages of this invention will become more apparent and understandable from the following detailed description, examples and claims.

DETAILED DESCRIPTION OF THE INVENTION

The bacteria which can be enumerated by using the present reagent are the bacteria related to periodontal diseases such as *Bacteroides melaninogenicus*, Capnocytophaga sp. and *Eikenella corrodens* which are gram-negative bacteria. They are usually found in the oral cavity.

An antiserum of the oral gram-negative bacteria used in this invention is prepared by injecting, for example subcutaneously, a pretreated strain of the oral gram-negative bacteria as an antigen to an animal such as a rabbit. For example, in the case of *Bacteroides melaninogenicus* subsp. *asaccharolyticus* #381, the strain which is treated with formalin and suspended with Freund's complete adjuvant is used as an antigen. In the case of Capnocytophaga sp. #4, the strain lysed by ultrasonic is used as an antigen. The antiserum of the present invention is an unlabelled antibody and is used for the treatment with a sample containing the gram-negative bacteria to be enumerated. The antiserum of this invention is high in antibody titer and does not show a cross-section with other species of bacteria.

The fluorescent conjugated antibody used in this invention is prepared by immunizing a different animal, for example a sheep if the antiserum is that of a rabbit, with γ-globulin of the same species as the antiserum obtaining an antibody, and then by labelling the antibody with fluorescence such as fluoresceinisothiocyanate or lissamine rhodamine. This fluorescent conjugated antibody is used for the treatment with the reaction product of the antiserum and a sample. As the result, the gram-negative bacteria to be enumerated are fluorescently detected and enumerated by observation under a fluorescent microscope.

The present reagent for enumeration of the bacteria related to periodontal diseases consists of the unlabelled antiserum and the fluorescent conjugated antibody. It is used for the detection and the enumeration of oral gram-negative bacteria, such as *Bacteroides melaninogenicus*, Capnocytophaga sp. and *Eikenella corrodens* in the oral cavity and other infected areas.

For the detection and the enumeration of these bacteria by using the present reagent, smears of a pretreated sample to be enumerated are treated with the antiserum. The smear is then treated with the fluorescent conjugated antibody, and the detection and enumeration are carried out by examining the fluorescent coated bacteria under a fluorescent microscope. In this case, it is preferable as the pretreatment of the sample to wash it with phosphate buffered saline adjusted to low pH for about ten minutes, because human immuno-globulins combined with bacteria can be separated by this treatment. The antiserum is usually diluted at a predetermined rate. This rate of dilution is not limited. However, for example, it is preferable to dilute the antiserum of Bacteroides melaninogenicus from 32 to 512 times, preferably from 128 to 256 times, and in the case of the antiserum of Capnocytophaga sp. it is preferable to dilute the antiserum from 64 to 512 times, preferably from 128 to 256 times. In the above-specified range of the dilution of the antiserum, only the bacteria to be enumerated are detected precisely. The reaction times of the antiserum with the smeared sample and of the antibody for with the product are preferably from 30 to 60 minutes.

The indirect fluorescent antibody method using the present reagent only needs a shortened period of time of about from 4 to 5 hours for the enumeration of the oral gram-negative bacteria in the sample and also gives essentially the same results as the usual cultural method. In contrast, the usual cultural method requires a long period of time of about a week or sometimes two weeks for the enumeration of the same bacteria. Accordingly, the oral gram-negative bacteria such as *Bacteroides melaninogenicus*, Capnocytophaga sp. and *Eikenella corrodens* are able to be enumerated rapidly and exactly by the use of the present reagent.

Moreover, the present method is very simple and is carried out in easy operation. The cost for the enumeration is half or less than the usual cultural method.

The following specific examples are further illustrative of the present invention, but it is to be understood that the invention is not limited thereto.

EXAMPLE

Rabbit antisera of *Bacteroides melaninogenicus* subsp. *asaccharolyticus* #381 and Capnocytophaga sp. #4 and an anti-rabbit serum (sheep) labelled with fluorescein-isothiocyanate (a fluorescent conjugated antibody) were prepared by the method mentioned below to obtain the reagents for the enumeration of the bacteria.
(A) Preparation of an antiserum of Bacteroides melaninogenicus subsp. asaccharolyticus #381

After *Bacteroides melaninogenicus* subsp. *asaccharolyticus* #381 was incubated anaerobicaly in Todd Hewitt broth (made by Difco Co. Ltd.) supplemented with 5 $\mu$g/ml of hemin, 0.5 $\mu$g/ml of menadione and 100 $\mu$g/ml of sodium succinate, the bacterial cells were collected by centrifugation and then washed 3 times by phosphate buffered saline (pH 7.0). All the bacterial cells were treated with formalin and suspended in Freund's complete adjuvant (made by Difco Co., Ltd.) at an equal weight ratio therewith.

The antigen thus obtained was injected subcutaneously into the hind paw of a rabbit. A second injection was carried out in the same manner after 3 weeks to increase the antibody titer. When the antibody titer increased more than 1024 times, a blood was collected by a cardiac stab and the blood clot was made by the ordinary method, followed by centrifugation of the supernatant to obtain the antiserum. This antiserum was preserved at $-14°$ C. after inactivating the complement by heating the antiserum at 56° C. for 30 minutes.
(B) Preparation of an antiserum of Capnocytophaga sp. #4

The antiserum was prepared by the same method as (A) except that bacterial cells lysed by ultrasonics were used as an antigen.
(C) Fluorescent conjugated antibody An anti-rabbit IgG globulin (sheep) labelled with fluorescein-isothiocyanate (made by Meloy Co., Ltd.) was used.

The enumeration technique using the reagents including the antiserum and the fluorescent conjugated anti-rabbit IgG globulin, and their results are explained as follows:

The enumeration of Bacteroides melaninogenicus and Capnocytophaga in subgingival plaque 28 subgingival plaque samples were taken from patients with periodontal diseases and healthy people. These plaque samples were suspended in 2 ml of pre-reduced anaerobically sterilized Ringer's solution with ultrasonics for 10 seconds. From 0.1 to 0.15 ml of the suspension were then dropped by a pipette on two circles (each diameter being about 1 cm) marked on a slide glass by a diamond marker, dried at room temperature and then thermally fixed by a burner. The smears thus obtained were washed with phosphate saline of pH 2.3 for 10 minutes and dried again at room temperature. One or two drops of the antiserum of *Bacteroides melaninogenicus* diluted to 32 times and that of Capnocytophaga sp. diluted to 128 times were added on the smears, respectively. The reaction was carried out at 37° C. for 30 minutes in a plastic box with a cover having a wet paper-towel therein. The reaction product was rinsed in phosphate buffered saline (pH 7.0) for 20 minutes and was then treated with the fluorescent conjugated anti-rabbit IgG globulin (the antibody) for 30 minutes. Afterwards, rinsings and dryings were repeated. The smears were treated with mounting fluid (made by Difco Co., Ltd.) of pH 7.2 to enumerate the bacteria under a fluorescent microscope (Carl Zeiss Microscope), where the microscope was 1000 magnifications (objective lens: $\times 100$, eye lens: $\times 10$), and BG 12 and BG 3 were used as excitation filters, and K500 was used as a barrier filter. The average number of fluorescent coated bacteria to the total number of bacteria in 2 views (area in which at least 100 bacteria existed per one view was selected) were enumerated under the microscope.

In order to compare the above method, enumeration of the bacteria by the cultural method was carried out as follows. The plaque samples from the patients with periodontal diseases and the healthy people were added to 2 ml of the pre-reduced anaerobically sterilized Ringer's solution, and the plaque samples were dispersed by a 10 second-treatment with ultrasonics. Tenfold serial dilutions of the sample suspension were prepared using the Ringer's solution, and 0.1 ml of from $10^{-2}$ to $10^{-5}$ times dilutions was poured on blood agar plates, followed by anaerobic incubation (80% $N_2$, 10% $H_2$, 10% $CO_2$) at 37° C. for 7 days. In the case of the enumeration of *Bacteroides melaninogenicus*, Todd Hewitt broth (made by Difco Co., Ltd.) 5% sheep blood agar supplemented with 5 $\mu$g/ml of hemin, 0.5 $\mu$g/ml of menadione and 100 $\mu$g/ml of sodium succinate was used as the agar plate. For the enumeration of Capnocytophaga sp., trypticase soy 5% sheep blood agar (made by BBL Co., Ltd.) was used. After the incubation, blood agar plates with colonies of from 50 to 100 were selected, and the enumeration was carried out by counting colonies with black pigment for *Bacteroides melaninogenicus* and wet spreading for Capnocytophaga sp. to total bacteria.

A part of the colonies was again enumerated by means of the above-mentioned indirect fluorescent antibody method for the confirmation. It was confirmed that the bacteria detected were the bacteria aimed at for the enumeration.

The results of the enumeration are shown in Table 1.

TABLE 1

| Sample No. | Age | Site | B.melaninogenicus to total bacteria (%) | | Capnocytophaga sp. to total bacteria (%) | |
|---|---|---|---|---|---|---|
| | | | IIF | Cultural method | IIF | Cultural method |
| 1 | 56 | 3 | 18 | 22 | 0 | 0 |
| 2 | 56 | 1 | 15 | 12 | 1 | 2 |
| 3 | 45 | 5 | 4 | 2 | 4 | 1 |
| 4 | 45 | 5 | 3 | 1 | 8 | 4 |
| 5 | 32 | 7 | 2 | 3 | 0 | 0 |
| 6 | 32 | 6 | 8 | 3 | 0 | 2 |
| 7 | 42 | 7 | 2 | 4 | 0 | 1 |
| 8 | 42 | 8 | 1 | 3 | 0 | 1 |
| 9 | 46 | 5 | 20 | 15 | 0 | 0 |
| 10 | 46 | 8 | 15 | 4 | 2 | 0 |
| 11 | 35 | 7, 8 | 5 | 0 | 5 | 3 |
| 12 | 35 | 5, 6 | 5 | 9 | 2 | 3 |
| 13 | 47 | 4 | 3 | 1 | 3 | 3 |
| 14 | 47 | 7 | 3 | 4 | 0 | 0 |
| 15 | 35 | 1 | 1 | 3 | 2 | 1 |
| 16 | 35 | 6 | 2 | 0 | 0 | 0 |
| 17 | 25 | 1 | 1 | 1 | 0 | 0 |
| 18 | 22 | 1 | 1 | 0 | 0 | 0 |
| 19 | 24 | 2 | 10 | 3 | 1 | 1 |
| 20 | 24 | 5 | 3 | 0 | 4 | 5 |
| 21 | 34 | 1 | 0 | 0 | 0 | 0 |
| 22 | 7 | 1 | 1 | 0 | 2 | 2 |
| 23 | 7 | 7 | 5 | 4 | 9 | 6 |
| 24 | 13 | 3 | 1 | 0 | 13 | 11 |
| 25 | 56 | 3 | 2 | 0 | 0 | 0 |
| 26 | 56 | 1 | 2 | 0 | 0 | 0 |
| 27 | 56 | 3 | 1 | 0 | 1 | 3 |
| 28 | 56 | 1 | 2 | 0 | 3 | 2 |

Note 1 : Site from which samples were taken.
Note 2 : IIF represents indirect fluorescent antibody technique.

A blind test was examined for the correlation coefficient between the indirect fluorescent antibody method and the cultural method. The results, 0.82 ($p<0.001$) for *Bacteroides melaninogenicus* and 0.87 ($p<0.001$) for Capnocytophaga sp., show a high correlation between the methods. Therefore, it was found from the above results that the indirect fluorescent antibody method using the present reagent can detect and enumerate precisely the bacteria such as *Bacteroides melaninogenicus* and Capnocytophaga sp.

The time required for the enumeration was reduced surprisingly according to the indirect fluorescent antibody method using the present reagent—which required only about 4 hours in comparison with the usual cultural method which requires a long period of time of about 7 days. The cost for the enumeration by the indirect fluorescent antibody method was less than a half of that of the cultural method.

Titers of the above-mentioned antisera against *Bacteroides melaninogenicus* subsp. *asaccharolyticus* #381, Capnocytophaga sp. #4 and *Eikenella corrodens* #1073S prepared by essentially the same method as (A) were studied by preparing twofold serial dilutions and by examining the cross-reaction with other strains of the same species. The results are shown in Tables 2 to 5.

Table 2 shows titers of antisera against *Bacteroides melaninogenicus* subsp. *asaccharolyticus* #381, Capnocytophaga sp. #4 and Eikenella corrodens #1073S. Table 3 shows titers of *Bacteroides melaninogenicus* subsp. *asaccharolyticus* #381 antiserum to three subspecies of *Bacteroides melaninogenicus* and the results of hemagglutination test. In Table 4, titers of Capnocytophaga sp. #4 antiserum to Capnocytophaga sp. with different biochemical characteristics are shown.

Titers of mixed antisera against *Eikenella corrodens* #1073S and #1083S prepared by the same method as mentioned above are shown in Table 5.

TABLE 2

| Microorganism | Titer | |
|---|---|---|
| | IIF | Agglutination method |
| *B.melaninogenicus* s.s. *asaccharolyticus* (#381) | 1024 | 1024 |
| Capnocytophaga sp. (#4) | 2048 | 1024 |
| *Eikenella corrodens* | | |

TABLE 2-continued

| Microorganism | Titer | |
|---|---|---|
| | IIF | Agglutination method |
| (#1073S) | 2048 | 1024 |

Note 3 : In agglutination method, the highest antiserum dilutions are shown at which at least heavy clumping occurred.

TABLE 3

| Subspecies (strain No.) | Titer | Hemagglutination test |
|---|---|---|
| asaccharolyticus | | |
| 381 | 1024 | + |
| 383 | 512 | + |
| 2013 | 1024 | + |
| 2015 | 1024 | + |
| 2019 | 1024 | + |
| 2050 | 1024 | + |
| BMD3 | 512 | + |
| melaninogenicus | | |
| 581 | 16 | − |
| ATCC 15930 | 8 | − |
| intermedius | | |
| 615 | 32 | − |
| 377 | 16 | − |
| 2203 | <2 | − |
| 2210 | <2 | − |

TABLE 4

| Capnocytophaga (strain No.) | Titer |
|---|---|
| 4 | 2048< |
| 25 | 1024 |
| 1101 | 2048< |
| 1102 | 512 |
| 3003 | 1024 |
| 3008 | 1024 |
| 4024 | 2048< |
| 4028 | 512 |

Note 4 : Capnocytophaga sp. #4 and #25 were isolated respectively from the patients with periodontitis and periodontosis. The other strains were isolated from children with destructive periodontal disease.

TABLE 5

| Eikenella corrodens (strain No.) | Titer of Mixed Antisera |
|---|---|
| 1073S | 4096 |
| 1006S | 1024 |
| 1080S | 1024 |
| 375 | 256 |
| 205L | 1024 |
| 211L | 1024 |
| 301L | 64 |
| 307L | 1024 |
| 406L | 256 |
| 408L | 512 |
| 501L | 512 |
| 505L | 128 |
| 601L | 512 |
| 605L | 128 |
| 608L | 128 |
| 612L | 512 |

Note 5 : Antisera were equivalently mixed by Eikenella corrodens 1073S and 1080S.

From the results shown in Table 2, it was found that antisera of *Bacteroides melaninogenicus* #381 and Capnocytophaga sp. #4 showed high titers of more than 1024 times by the indirect fluorescent antibody method and also by the agglutination method.

As shown apparently in Table 3, antiserum of *Bacteroides melaninogenicus* subsp. *asaccharolyticus* #381 cross-reacted with 7 strains of subspecies *asaccharolyticus*, but did not cross-react with strains of subspecies *melaninogenicus* and *intermedius*. This was in agreement with the result of the hemagglutination test related to plus-like structure of bacterial cell surface. It was found from the above results that the use of #381 antiserum gave precise detection and enumeration of strains of subspecies *asaccharolyticus*. It was also found from the results of Table 4 that Capnocytophaga sp. #4 antiserum was cross-reacted in titers of more than 512 times with other strains of Capnocytophaga sp. isolated from the patients with different periodontal diseases and having different biochemical characteristics. Table 5 shows that mixed antisera of *Eikenella corrodens* #1073S and #1080S also gives high titers.

Accordingly, it is understandable that the reagent according to the present invention can detect and enumerate precisely oral gram-negative bacteria such as *Bacteroides melaninogenicus*, Capnocytophaga sp. and *Eikenella corrodens*.

What is claimed is:

1. A method for the enumeration of oral gram-negative bacteria selected from the group consisting of *Bacteroides melaninogenicus* and Capnocytophaga sp. by an indirect fluorescent antibody method comprising the steps of:
   (a) preparing a smear of a sample containing bacteria selected from the group consisting of *Bacteroides melaninogenicus* and Capnocytophaga sp.;
   (b) pretreating said smear with phosphate buffered saline, having a low pH, to remove human immuno-globulins combined with said bacteria;
   (c) treating said sample with an unlabelled antiserum selected from the group consisting of an antiserum to *Bacteroides melaninogenicus* which is diluted from 32 to 512 times and an antiserum to Capnocytophaga sp. which is diluted from 64 to 512 times, the antiserum to *Bacteroides melaninogenicus* being prepared by treating the bacterial cells with formalin, suspending the treated cells in Freund's complete adjuvant to obtain an antigen and injecting the antigen subcutaneously into a rabbit and collecting the antiserum from the rabbit and the antiserum to Capnocytophaga sp. being prepared by lysing the Capnocytophaga sp. bacterial cells by ultrasonic treatment, treating the lysed cells with formalin and suspending the treated cells in Freund's complete adjuvant to obtain an antigen and injecting the antigen subcutaneously into a rabbit and collecting the antiserum from the rabbit;
   (d) treating the reaction product of the sample and the antiserum with a fluorescent conjugated antibody obtained by immunizing a different species of animal with $\gamma$-globulin of the same species of animal as the antiserum and labelling the obtained antibody to said $\gamma$-globulin with a fluorescent substance; and
   (e) enumerating the oral gram-negative bacteria by observation under a fluorescent microscope.

2. The method according to claim 1, wherein said unlabelled antiserum is an antiserum to *Bacteroides melaninogenicus* subspecies *asaccharolyticus*.

3. The method according to claim 1, wherein said unlabelled antiserum is an antiserum to Capnocytophaga sp. #4.

4. The method according to claim 2 or 3, wherein said phosphate buffered saline is adjusted to a pH of about 2.3.

* * * * *